United States Patent
Shapira (10) Patent No.: US 12,151,125 B2
(45) Date of Patent: Nov. 26, 2024

(54) MAGNETIC RESONANCE (MR) PERFORMANCE IN MR-GUIDED ULTRASOUND SYSTEMS

(71) Applicant: Boaz Shapira, Tirat Carmel (IL)

(72) Inventor: Boaz Shapira, Tirat Carmel (IL)

(73) Assignee: INSIGHTEC LTD., Tirat Carmel (IL)

( * ) Notice: Subject to any disclaimer, the term of this patent is extended or adjusted under 35 U.S.C. 154(b) by 292 days.

(21) Appl. No.: 17/613,168

(22) PCT Filed: Jun. 5, 2020

(86) PCT No.: PCT/IB2020/000458
§ 371 (c)(1),
(2) Date: Nov. 22, 2021

(87) PCT Pub. No.: WO2020/245660
PCT Pub. Date: Dec. 10, 2020

(65) Prior Publication Data
US 2022/0203139 A1 Jun. 30, 2022

Related U.S. Application Data

(60) Provisional application No. 62/858,127, filed on Jun. 6, 2019, provisional application No. 62/858,129, filed
(Continued)

(51) Int. Cl.
*A61N 7/02* (2006.01)
*A61B 90/00* (2016.01)
(Continued)

(52) U.S. Cl.
CPC .............. *A61N 7/02* (2013.01); *A61B 90/36* (2016.02); *G01R 33/341* (2013.01);
(Continued)

(58) Field of Classification Search
CPC .............. A61N 7/02; A61N 2007/0065; A61N 2007/0078; A61N 2007/0095;
(Continued)

(56) References Cited

U.S. PATENT DOCUMENTS

2010/0019764 A1* 1/2010 Zahn ................ G01R 33/34046
324/309
2010/0259259 A1* 10/2010 Zahn .................. G01R 33/5601
324/309
(Continued)

FOREIGN PATENT DOCUMENTS

JP 2013-519495 5/2013
JP 2015-534488 12/2015
(Continued)

OTHER PUBLICATIONS

International Search Report and Written Opinion, dated Sep. 23, 2020, for the Corresponding International Patent Application No. PCT/IB2020/000458, 12 pages.
(Continued)

*Primary Examiner* — Dixomara Vargas
(74) *Attorney, Agent, or Firm* — MORGAN, LEWIS & BOCKIUS LLP (57) ABSTRACT

Ultrasound transducers adjust the $B_1^+$ and/or $B_1^-$ field distribution in an MRI apparatus to improve the signal sensitivity and homogeneity at a region of interest. Approaches employed include strategic placement of field-altering features such as slots and/or dipoles along the exterior surface or, in some cases, the interior of the transducer. In various embodiments, the field-altering features are (or behave as) passive resonators.

20 Claims, 8 Drawing Sheets

Related U.S. Application Data on Jun. 6, 2019, provisional application No. 62/858,409, filed on Jun. 7, 2019, provisional application No. 62/858,410, filed on Jun. 7, 2019, provisional application No. 62/862,995, filed on Jun. 18, 2019, provisional application No. 62/862,996, filed on Jun. 18, 2019.

(51) Int. Cl.
*G01R 33/341* (2006.01)
*G01R 33/48* (2006.01)
*A61B 90/50* (2016.01)
*A61N 7/00* (2006.01)

(52) U.S. Cl.
CPC .... *G01R 33/4814* (2013.01); *A61B 2090/374* (2016.02); *A61B 2090/502* (2016.02); *A61N 2007/0065* (2013.01); *A61N 2007/0078* (2013.01); *A61N 2007/0095* (2013.01)

(58) Field of Classification Search
CPC .............. A61B 90/36; A61B 2090/374; A61B 2090/502; G01R 33/341; G01R 33/4814
See application file for complete search history.

(56) References Cited

U.S. PATENT DOCUMENTS

| | | | |
|---|---|---|---|
| 2011/0034800 | A1 | 2/2011 | Vitek et al. |
| 2011/0270136 | A1* | 11/2011 | Vitek ........................ A61N 7/02 601/2 |
| 2012/0289869 | A1* | 11/2012 | Tyler ........................ A61B 5/245 601/2 |
| 2015/0246249 | A1* | 9/2015 | Tolo .......................... A61N 7/02 601/3 |
| 2015/0334487 | A1* | 11/2015 | Bowers ................. G10K 11/345 367/138 |
| 2019/0021666 | A1* | 1/2019 | Hynynen .................. A61B 6/03 |
| 2020/0360733 | A1* | 11/2020 | Yan ..................... G01R 33/5659 |
| 2021/0170204 | A1* | 6/2021 | Vortman .................. A61N 7/02 |

FOREIGN PATENT DOCUMENTS

| | | |
|---|---|---|
| JP | 2016-508808 | 3/2016 |
| JP | 2019-51599 | 4/2019 |
| WO | 2012137179 | 10/2012 |
| WO | 2014053950 | 4/2014 |
| WO | 2017143444 | 8/2017 |

OTHER PUBLICATIONS

Notice of Reasons for Rejection, dated Dec. 13, 2022 in corresponding Japanese Patent Application No. 2021-571691, 11 pages.
Alipour, A. et al: "An inductively coupled ultra-thin, flexible, and passive RF resonator for MRI marking and guiding purposes: Clinical feasibility : Ultra-Thin, Flexible, Passive RF Resonator Marker for MRI", Magnetic Resonance in Medicine., vol. 80, No. 1, Jul. 1, 2018 (Jul. 1, 2018), pp. 361-370, XP055730618, US, ISSN: 0740-3194, DOI: 10.1002/mrm.26996.

* cited by examiner

MAGNETIC RESONANCE (MR) PERFORMANCE IN MR-GUIDED ULTRASOUND SYSTEMS

CROSS-REFERENCE TO RELATED APPLICATION

This Application is a United States National Stage Application filed under 35 U.S.C. § 371 of PCT Patent Application Serial No. PCT/IB2020/000458, filed on Jun. 5, 2020, which claims priority to and the benefit of U.S. Provisional Patent Application No. 62/858,410, filed on Jun. 7, 2019; U.S. Provisional Patent Application No. 62/858,127, filed on Jun. 6, 2019; U.S. Provisional Patent Application No. 62/858,129, filed on Jun. 6, 2019; U.S. Provisional Patent Application No. 62/862,995, filed on Jun. 18, 2019; U.S. Provisional Patent Application No. 62/858,409, filed on Jun. 7, 2019; and U.S. Provisional Patent Application No. 62/862,996, filed on Jun. 18, 2019 Each of these applications is hereby incorporated by reference in its respective entirety.

FIELD OF THE INVENTION

The present invention relates, generally, to magnetic resonance-guided (MR-guided) focused ultrasound systems and methods.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

An MRI device uses powerful magnets to produce a strong magnetic field that forces protons in the body to align with that field. When a radiofrequency (RF) current is then pulsed through the patient, the protons are stimulated, and when the RF field is turned off, one or more receiver coils detect the energy released as the protons realign with the magnetic field. The time it takes for the protons to realign with the magnetic field, as well as the amount of energy released, depend on the environment and the chemical nature of the molecules. These differences can be exploited to reconstruct a 3D image of a region of interest (ROI) within the patient.

The combination of modalities—MRI and focused ultrasound—means that, in particular, the MRI images that are created under the MRI scanner cannot be disturbed by or interact excessively with the transducer elements that create focused ultrasound, since the ultrasound transducer will necessarily be disposed within the magnetic elements.

SUMMARY

Embodiments of the invention adjust the $B_1^+$ and/or $B_1^-$ field distribution to improve the signal sensitivity and homogeneity at the ROI. Approaches employed herein include strategic placement of field-altering features such as slots and/or dipoles along the exterior surface or, in some cases, the interior of the transducer. In various embodiments, the field-altering features are (or behave as) passive resonators.

Accordingly, an aspect of the invention relates to an ultrasound transducer for use with an MRI unit having at least one transmit coil and at least one receive coil. In various embodiments, the ultrasound transducer comprises a dielectric layer and, conforming to at least a portion thereof, a first conductive layer having at least one passive resonator thereon or therethrough, where the passive resonator has a geometry and dimensions selected to achieve an optimized $B_1^+$ and/or $B_1^-$ magnetic field distribution within a field of view of the MRI transmit and/or receive coil. The optimized magnetic field distribution may be maximal $B_1^+$ and/or $B_1^-$ homogeneity and/or sensitivity in a region of interest.

In some embodiments, the passive resonator(s) are at least one elongated slot through the conductive layer and extending across at least a portion thereof. The slot(s) may be, for example, a pair of slots in a cruciform configuration. In some embodiments, the slot(s) are filled with a metamaterial element. The passive resonator(s) may be composed of a material having a dielectric constant in excess of 10 and attached to the surface of the transducer. In some embodiments, the passive resonator(s) are dipoles. The geometry, location and/or orientation of the passive resonator(s) may be adjustable. In some embodiments, the resonator(s) are shaped as a loop, dipole, or figure-8. The passive resonator(s) may be disposed on the interior surface of the transducer at an interface with a dielectric medium.

In various embodiments, the dielectric and first conductive layer are substantially hemispheric. In other embodiments, the conductive layer comprises a plurality of discrete conductive elements tiled in a mosaic fashion. The transducer may further comprise at least one additional conductive region spaced apart from the first conductive region but also conforming to the dielectric layer. The first conductive layer may have at least two passive resonators thereon or therethrough. At least one of the passive resonators may have a dielectric constant in excess of 10 and may be attached to the surface of the transducer, and at least one passive resonator may be one or more elongated slots through the conductive layer and extending across at least a portion thereof. At least one passive resonator may be disposed an external area of the transducer, e.g., a bottom ring surface configured to surround a patient's head. For example, the passive resonator(s) may be a foil sheet or a mesh.

BRIEF DESCRIPTION OF THE DRAWINGS

The foregoing and the following detailed description will be more readily understood when taken in conjunction with the drawings, in which.

DETAILED DESCRIPTION

Figure 1A:
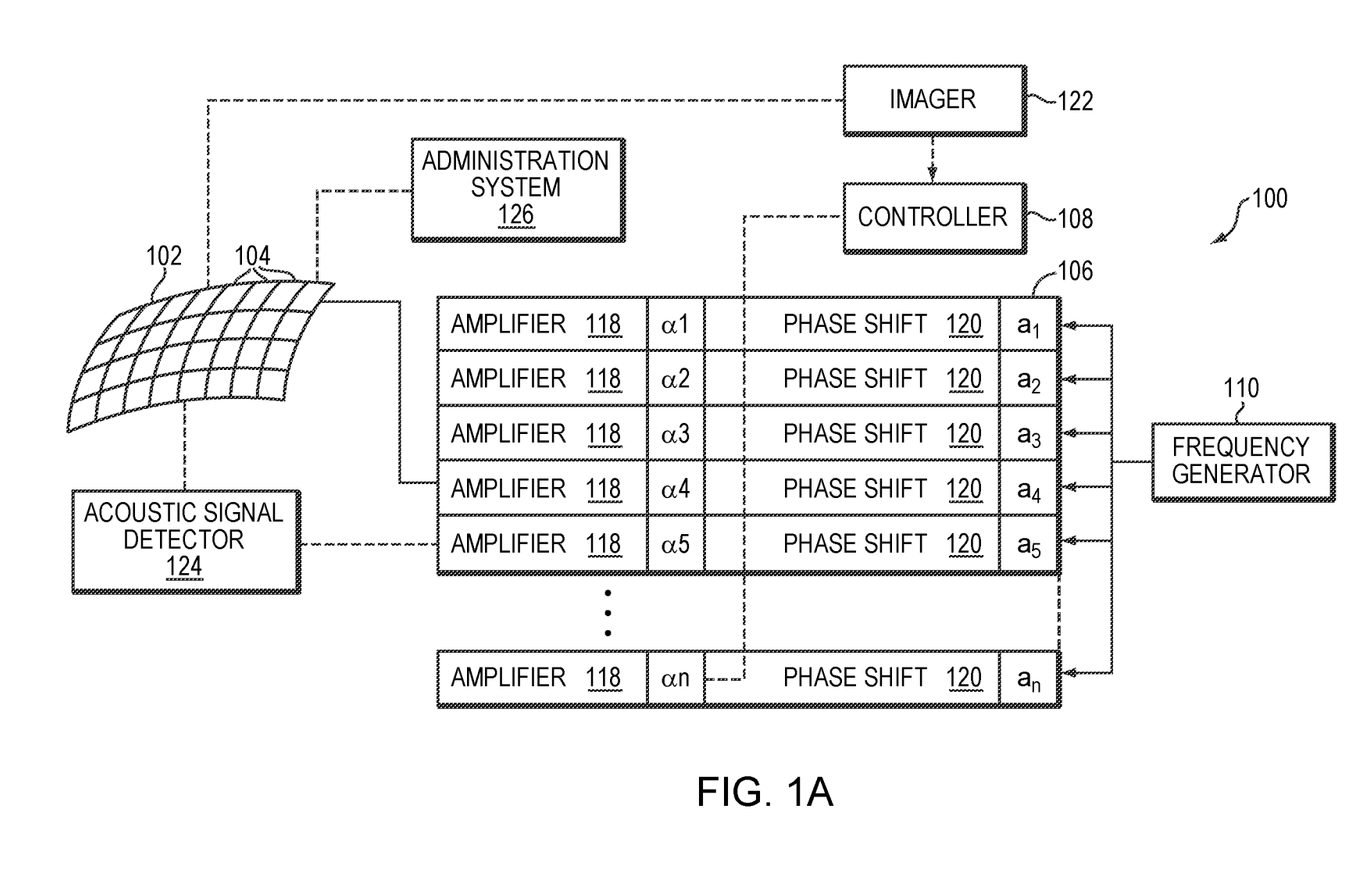
FIG. 1A schematically illustrates an exemplary focused ultrasound system in accordance with various embodiments.

Refer first to FIG. 1A, which illustrates an exemplary ultrasound system 100 for generating and delivering a focused acoustic energy beam to a target region for disrupting the tissue and thereby causing the tissue permeability to increase therein. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on the surface of the patient's body, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50 Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radiofrequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radiofrequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy onto the target region, and account for wave distortions induced in the tissue located between the transducer elements 104 and the target region. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial field patterns at the target region. In certain embodiments, the computation is based on detailed information about the characteristics (e.g., structure, thickness, density, etc.) of the intervening tissue located between the transducer element 104 and the target and their effects on propagation of acoustic energy. Such information may be obtained from an imager 122. The imager 122 may an MRI device as discussed below.

Figure 1B:
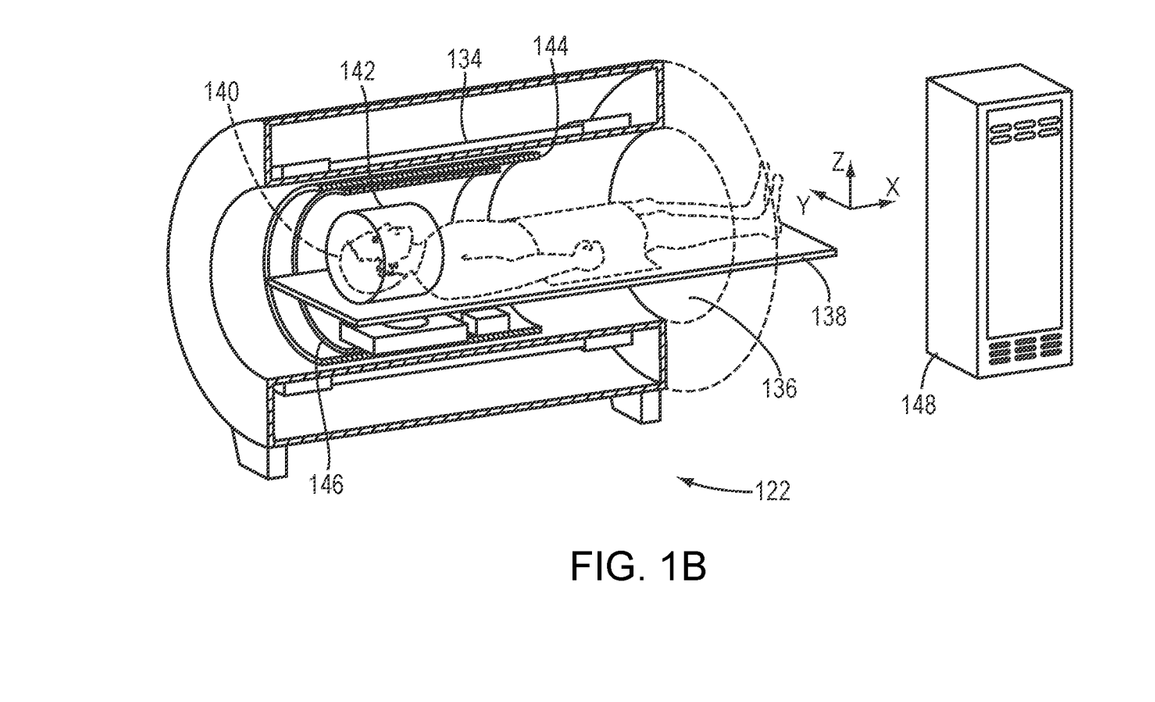
FIG. 1B illustrates an MRI system in accordance with various embodiments.

FIG. 1B illustrates an exemplary MRI apparatus 122. The apparatus 122 may include a cylindrical electromagnet 134 (or a permanent magnet), which generates a static magnetic field within a bore 136 of the electromagnet 134. In MRI, the nuclear spins within the body tissues interact with the external magnetic field, processing around the magnetic field with a particular resonance frequency also known as Larmor frequency, $\omega_0 = \gamma B$, where B in this case is the external magnetic field and $\gamma$ is the gyromagnetic ratio, which is a property of the nuclear spin. During medical procedures, a patient is placed inside the bore 136 on a movable support table 138. A region of interest (ROI) 140 within the patient (e.g., the patient's head) may be positioned within an imaging region 142 wherein the electromagnet 134 generates a static magnetic field, $B_0$, with spatial homogeneity of a few parts per million. A set of cylindrical magnetic field gradient coils 144 may also be provided within the bore 136 and surrounding the patient. The gradient coils 144 generate magnetic field gradients of predetermined magnitudes, at predetermined times, and in three mutually orthogonal directions. With the field gradients, different spatial locations can be associated with different precession frequencies, thereby giving an MR image its spatial resolution. The MRI data can be obtained only by exciting the spin system within the tissues out of magnetic equilibrium and measuring the excited spin system signal. In order to excite the spins, an RF transmitter coil 146 surrounding the imaging region 142 emits shaped RF pulses at a frequency, $\omega_{rf}$ into the imaging region 142 to cause the patient's tissues to emit magnetic-resonance (MR) response signals. The shaped RF pulses elicit a frequency-response profile centered around $\omega_{rf}$ with a finite effective width $\Delta\omega_{rf}$. Only spins that precess near $\omega_{rf}$ within the effective width $\Delta\omega_{rf}$ will be excited by the RF pulse. Raw MR response signals are sensed by the RF coil 146 and passed to an MR controller 148 that then computes an MR image, which may be displayed to the user. Alternatively, separate MR transmitter and receiver coils may be used. Images acquired using the MRI apparatus 122 may provide radiologists and physicians with a visual contrast between different tissues and detailed internal views of a patient's anatomy that cannot be visualized with conventional x-ray technology.

The MRI controller 148 may control the pulse sequence, i.e., the relative timing and strengths of the magnetic field gradients and the RF excitation pulses and response detection periods. The MR response signals are amplified, conditioned, and digitized into raw data using a conventional image-processing system, and further transformed into arrays of image data by methods known to those of ordinary skill in the art. Based on the image data, the target region (e.g., a tumor) can be identified.

Figure 1C:
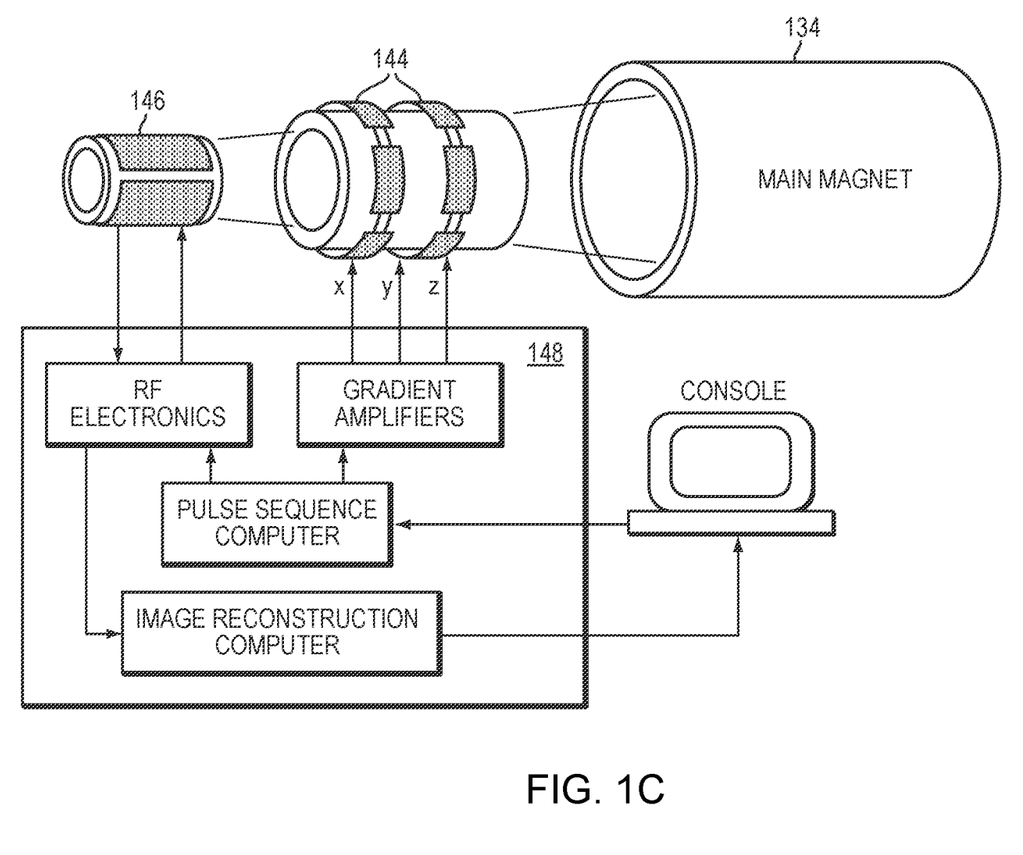
FIG. 1C schematically illustrates the primary operative components of an MRI device in greater detail.

The primary operative components of an MRI device are illustrated in greater detail in FIG. 1C. The main magnet 134, which may be, e.g., 3T in strength, produces the $B_0$ field to align the spins and achieve equilibrium. The gradient coils 144 enable image encoding in the x, y, and z directions (i.e., the frequency, phase, and slice-encoding directions). The RF coils 146 transmit and receive signals, exciting the aligned spins and receiving the RF signal from the ROI. As a patient is positioned in an MRI scanner, the tissue obtains a small magnetization that aligns with the magnetic field, $M_0$. An RF transmit (Tx) coil generates an RF pulse that produces a small magnetic field, $B_1$, which is mostly perpendicular to the main magnetic field $B_0$. Only the perpendicular magnetic field components, $B_1^+$ which oscillate around the spin's resonance frequency, will effectively rotate net magnetization away from its alignment with the main magnetic field. The stronger the RF pulse (energy), the farther the magnetization will tilt or flip. The RF receive (Rx) coil detects the precessing magnetization resulting in an induced electric current via electromagnetic induction. The induced current is the MR signal, and represents the mixture of the magnetizations from the tissue within the field of view (FOV) of the Rx coil. The scanner may have multiple coils for both transmit and receive functions.

The Tx coils generate the electromagnetic $B_1^+$ field, which is designed to be perpendicular to the main (static) magnetic field $B_0$, and oscillates at the resonance frequency, $\gamma B_0$, in an elliptically polarized mode. The precession frequency corresponds to the frequency range of radio waves (MHz). The received electromagnetic field, which is also perpendicular to $B_0$, is referred to as the $B_1^-$ field.

A single "body coil" can alternately serve as transmitting and receiving coil, generating the $B_1^+$ field and sensing the $B_1^-$ field. The delivered $B_1^+$ field should be homogeneous over the FOV to promote homogeneous excitation, and the coil should possess high sensitivity across the ROI (which is smaller than or equal to the FOV area). The body coil is configured for operation with the patient lying in the bore 136 shown in FIG. 1B. The introduction of the transducer array 102 within the bore 136 can disrupt both homogeneity and sensitivity. Specifically, the geometry of the transducer array 102 and its dielectric properties (which arise mainly from highly electrically conductive components and a dielectric liquid such as water) may vary the spatial distribution of electromagnetic energy within the bore 136; in effect, the transducer array 102 acts as a resonator cavity, imposing frequency-dependent mode patterns.

Figure 2A:
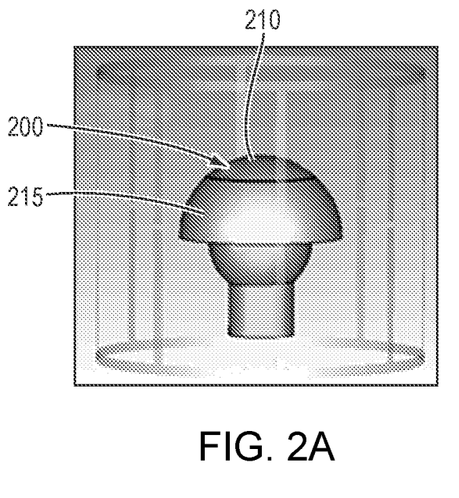
FIGS. 2A and 2C are perspective view of, respectively, a two-piece curved transducer design and a mosaic transducer design in accordance with embodiments of the invention.
Figure 2B:
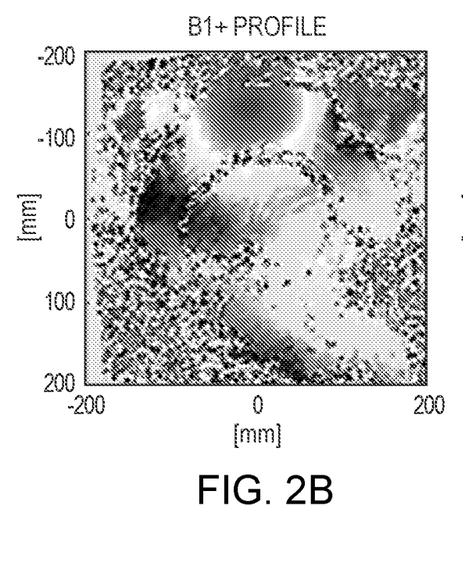
FIGS. 2B and 2D are sagittal cranial slices illustrating the inhomogeneities resulting from the transducer geometries shown in FIGS. 2A and 2C, respectively.
Figure 2C:
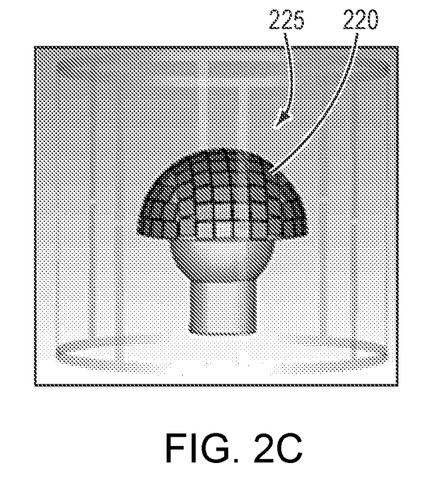

For cranial imaging, the ultrasound transducer may have a simple configuration as a two-element curved hemisphere 200 shown in FIG. 2A, which includes a domed top element 210 separated from a bottom skirt element 215 by a narrow annular gap. Alternatively, the ultrasonic transducer may comprise or consist of tile-like elements 220 arranged in a mosaic fashion to approximate a hemisphere 225, as shown in FIG. 2C.

Figure 2D:
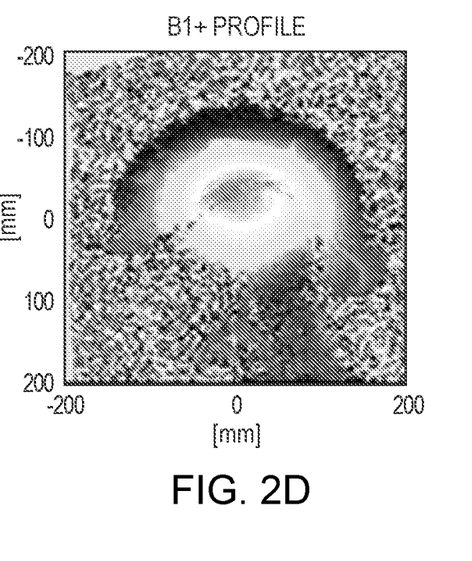
Figure 2E:
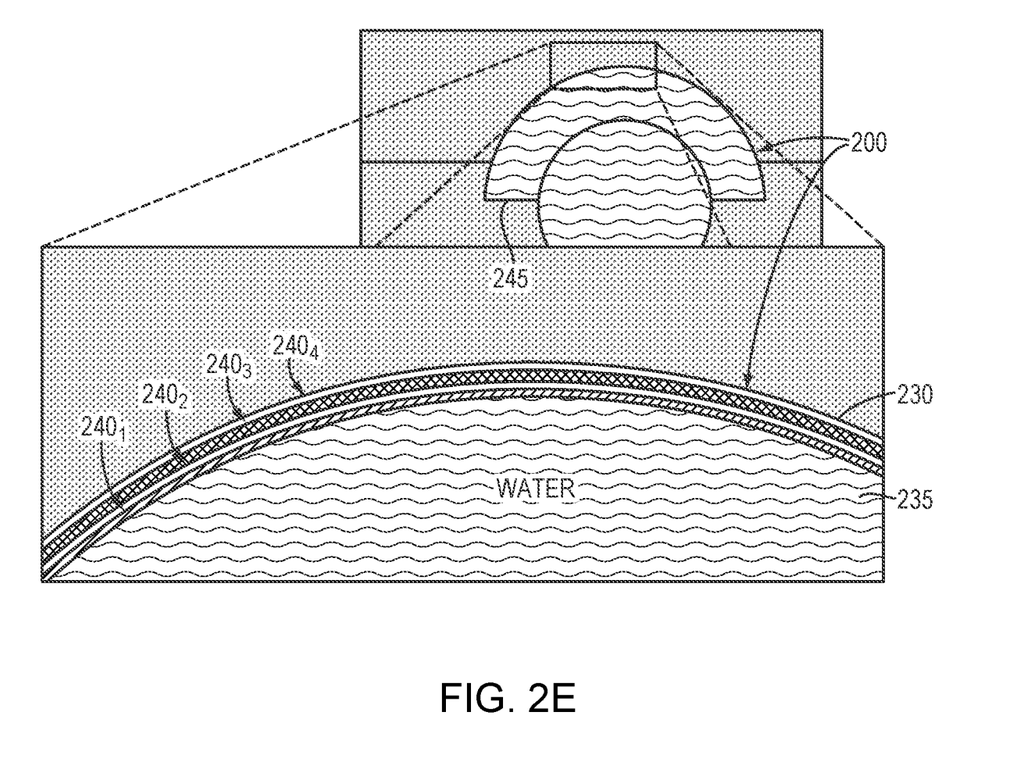
FIG. 2E is a sectional view of a multi-layer transducer construction.

In some embodiments, the transducer may include more than a single highly electrically conductive layer through its thickness. A representative construction is shown in FIG. 2E, in which the transducer 200 has a four-layer membrane 230 encapsulating and defining a water-filled chamber 235. The membrane 230 includes an innermost polymeric (e.g., silicone) layer $240_1$ which may be, for example, 1 mm in thickness; a first conductive (e.g., copper) layer $240_2$, which may have a thickness of 2 mm; a second polymeric layer $240_3$, which may again be 1 mm in thickness; and a second (and outermost) conductive layer $240_4$ which may have a thickness of 0.1 mm. Typically the slot will extend through all of the highly electrically conductive layers, so for the embodiment shown in FIG. 2E, it may extend through layers $240_2$, $240_4$ but not necessarily through the polymeric layers $240_1$, $240_3$. In some embodiments, the slots (or notches) can be filled with passive resonators such as metamaterial components (e.g., capacitive and inductive elements) with sub-$\lambda$ size (where $\lambda$ is the RF wavelength within the water), which will vary the impedance of the dielectric shell and will vary the electromagnetic field distribution therein.

Electromagnetic waves interacting with the highly electrically conductive material are reflected. Reflection from the inner side of the hemisphere produces a standing wave with poor $B_1^+$ pattern at the ROI, as shown in FIG. 2B. A simplified description of the phenomenon uses a reflection coefficient $\Gamma$ defined between two layers; for example, in the case of water and copper layers, $$\Gamma = \frac{Z_c - Z_w}{Z_c + Z_w},$$

where $Z_w$ and $Z_c$ are the water and copper impedances, respectively. Since $Z_w \gg Z_c$, the reflection is about $\Gamma = -1$, which implies a total reflection of the wave with a flipped sign that produces maximal $B_1^+$ intensity at the domed element 210 and minimal $B_1^+$ intensity therebelow as shown in FIG. 2B.

Figure 3A:
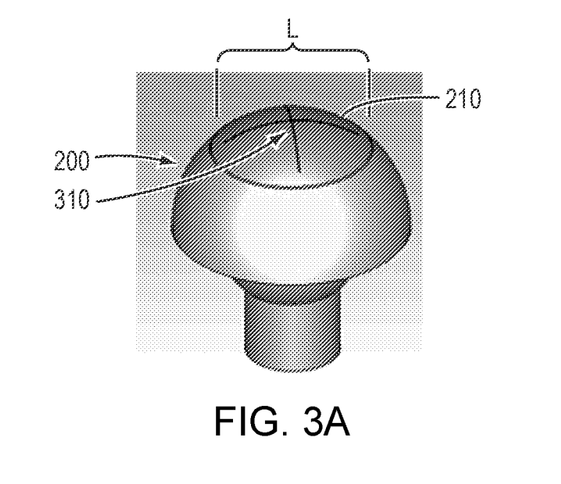
FIG. 3A is a perspective view of a curved transducer design including two slots.

In an embodiment particularly useful with the curved-hemisphere configuration 200, the field disruption is reduced by introducing one or more slots 310 through the highly electrically conductive (e.g., copper) layer as shown in FIG. 3A. This effectively creates a slot antenna, which allows RF penetration between the inside and the outside of the hemisphere 200 and rearranges the $B_1$ field inside the transducer. The slots 310 may be filled with a low-conductivity material (e.g, air or polymer). In some embodiments, slots are introduced in the domed top element 210 as shown in FIG. 3A; in the skirt element 215; or in both elements 210 and 215.

Figure 3B:
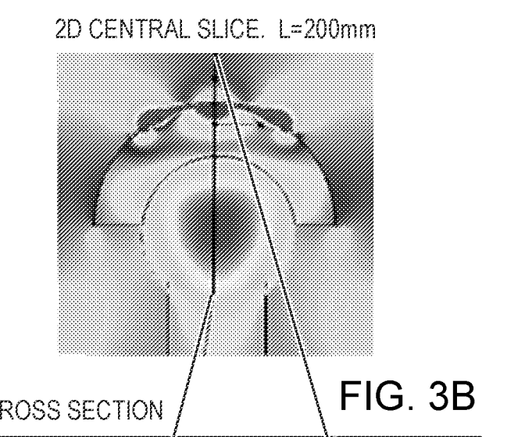
FIGS. 3B and 3C shows the $B_1^+$ field computed via simulation using two perpendicular, cruciform slots having a uniform width of 1 mm and a length L of 200 mm and 172 mm, respectively.
Figure 3C:
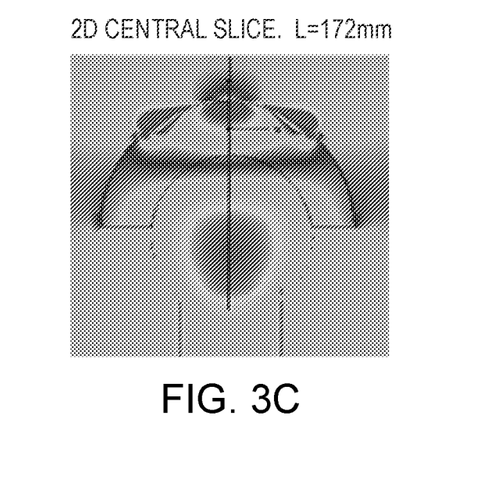
Figure 3D:
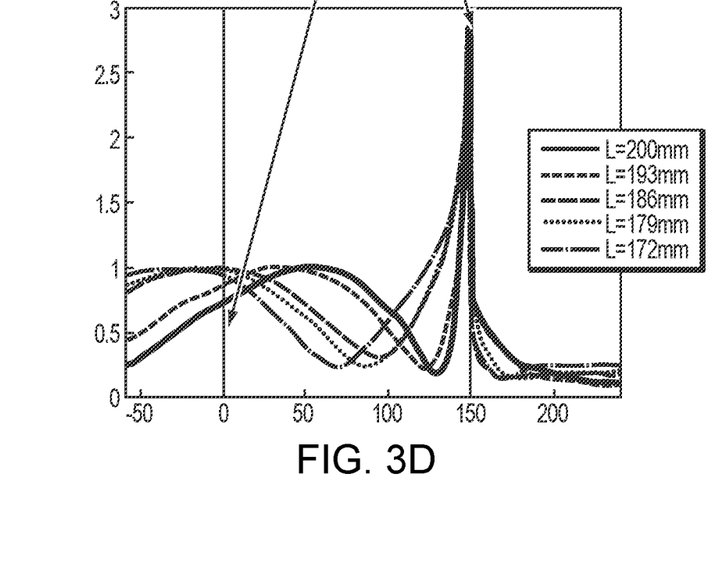
FIG. 3D graphically depicts the $B_1^+$ distributions resulting from different slot lengths.

Cutting cruciform slots 310 through the highly electrically conductive shell as shown in FIG. 3A, under restorative conditions, allows RF waves to penetrate the highly electrically conductive shell between the inside and the outside of the transducer. The optimal geometry and lengths of the slots may be selected, without undue experimentation, through simulation or actual measurement in order to achieve a desired $B_1^+$ pattern. Using two perpendicular, cruciform slots having a uniform width of 1 mm and a length L of 172 mm, the resulting $B_1^+$ field computed via simulation is shown in FIG. 3C. (The result for a 200 mm slot length is shown in FIG. 3B). FIG. 3D illustrates the $B_1^+$ distributions resulting from different slot lengths L; accordingly, it is straightforward to design slot geometries and select among them to achieve the desired pattern. In particular, it may be desired to have the relatively flat (and therefore maximally homogeneous) leftmost peak region in the FOV or ROI.

While the objective is to manipulate the $B_1^+$ and/or $B_1^-$ pattern within the transducer, a strong dependency between the slot geometry and the field distribution is observed when adjacent transducer layers (e.g., air, copper, water) have matched impedance values. The effect of a linear slot element can be qualitatively approximated as the effect of a linear slot antenna surrounded by a conductive sheet, which linearly polarizes electromagnetic radiation above a cutoff frequency. Two perpendicular slots 310 will impose two perpendicular linear polarizations on the electromagnetic radiation, resulting in elliptical polarization (EP) that maintains the phase from the source electromagnetic wave, either from the transmitted RF elliptical polarized pulse, $B_1^+$, or from the spin system signal, $B_1^-$. The Tx/Rx signal of the combined body coil and slot antennas result in two coherent sources for $B_1^+$, $B_1^-$ that interfere to produce a new $B_1^+$, $B_1^-$ pattern. The lengths of the slots can be adjusted to change the elliptical polarization. For Tx, the slots impose a passive "RF shimming" at the FOV or ROI. For Rx, they improve the signal sensitivity and homogeneity at the ROI. In general, other slots or notches can be imposed along the sides of the transducer to further manipulate the $B_1^+$ pattern. In some embodiments, each slot has an adjustable geometry to improve the field distribution in region of interest (e.g., part of the slot can be covered with a conducting sheet). The adjustment can be triggered by, for example, the initial MRI images. In one approach, a conducting sheet is slidably situated within guides so that a desired amount of a slot can be covered.

Figure 4A:
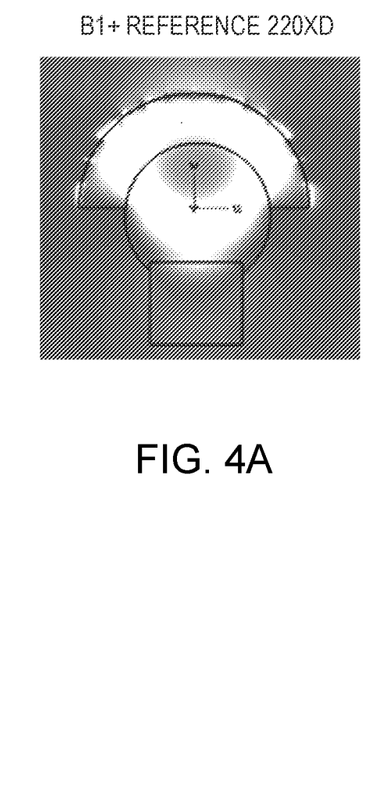
FIGS. 4A and 4C are comparative simulations illustrating the $B_1^+$ fields produced by transducers as shown in FIG. 4B with and without dipoles.
Figure 4B:
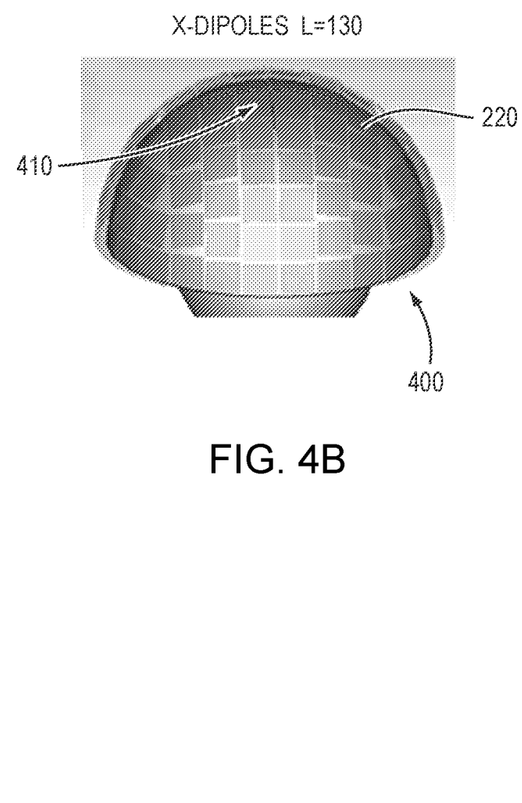
FIG. 4B is a perspective view of a mosaic transducer design including two dipoles.
Figure 4C:
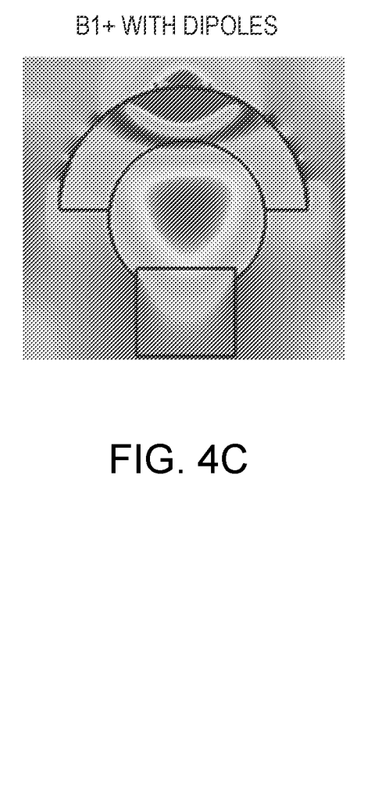

Similar to the slot antenna configuration, a passive resonator approach is applicable to other transducer configurations such as the mosaic transducer design, as illustrated in FIGS. 4A-4C. The mosaic configuration allows RF from the body coil to pass through the transducer 400, but the boundaries between the water within the transducer 400 and air reflect the RF and can still cause inhomogeneities in the signal intensity at the center of the transducer base, as illustrated in FIGS. 2D and 4A. Using a simplified description for RF propagation, the reflection coefficient between water and air in the mosaic transducer 400 is $\Gamma \approx 1$, meaning that the RF still behaves as a standing wave within the transducer.

Based on the Babinat principle, a slot antenna in a curved transducer and a dipole antenna in a mosaic transducer will exhibit similar RF radiation effects. Hence, adding one or more dipoles 410 to the surface of the mosaic transducer 400 will affect transducer behavior in a manner analogous to adding a slot antenna on a curved transducer. The dipoles 410—strings or strips composed of electrically conductive material such as copper—serve as passive resonators that beneficially shift the region of $B_1^+/B_1^-$ field homogeneity toward the ROI. The length, width and geometry of the dipoles can be straightforwardly adjusted in order to manipulate the $B_1^+/B_1^-$ field homogeneity. The dipoles 410 can be isolated from other conductive layers (e.g., copper or other metal or electrically conductive material), tiles and the underlying dielectric layer, and electrically isolated from the transducer, by including a layer of adhesive or polymer under the dipoles. It should be appreciated that in addition to achieving field homogeneity, the resonators should be substantially to the transparent to the ultrasound waves emitted by the transducer 200. This may be achieved by keeping the resonator widths small (e.g., ranging from submillimeter widths to a few mm) and/or positioning them away from the ultrasound propagation medium. With reference to FIG. 2E, the dipoles may reside on the exposed (interior) surface of the nonconductive layer $204_1$. Alternatively, the dipoles can be isolated by plastic (or other dielectric material) and not in direct contact with the water.

Figure 5A:
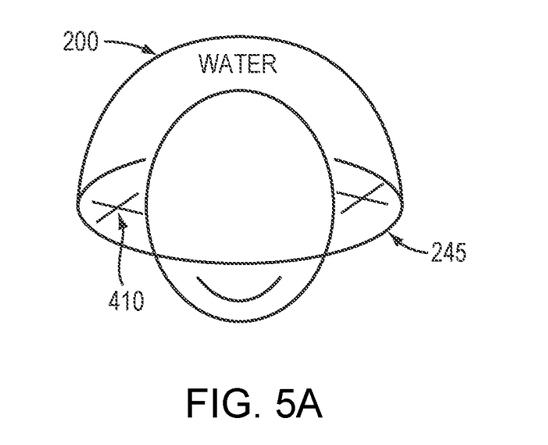
FIG. 5A is a transparent perspective view of a transducer with dipoles disposed on an underlying surface.
Figure 5B:
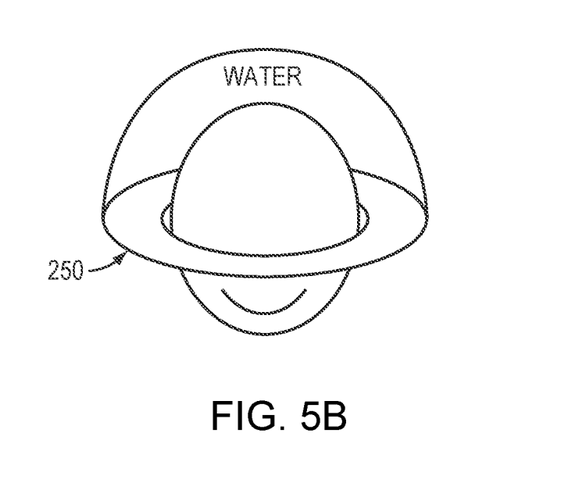
FIG. 5B is a transparent perspective view of a transducer with a sheet resonator disposed on an underlying surface.

In some embodiments, a set of passive resonators with loop geometries (e.g., circles, ellipses, or figure-8s) and/or dipole (elongated) shapes and/or other geometric shapes that affect the RF field within the FOV can be disposed at the surface of the transducer 200. In this context, a passive resonator means an element having a high (e.g., >10) dielectric constant. In other embodiments, as illustrated in FIG. 5A, passive resonators (e.g., dipoles 410) can be added along the underlying surface 245 (see also FIG. 2E) of the transducer 200 that surrounds the patient's head, as an alternative or in addition to the passive resonators at the upper surface of the transducer. In this case, the underlying surface 245 is nonconductive (e.g., polymeric) and the dipoles may be on the interior (in contact with the dielectric liquid) or exterior of the underlying surface. Another alternative is to make the interior or exterior of the entire underlying surface 245 conductive using, for example, a copper or aluminum foil or mesh 250 as shown in FIG. 5B.

Again, the passive resonator may be adjustably configured so that the geometry, location and/or orientation of the resonator can be altered to improve the field distribution in the ROI. The adjustment can be triggered, for example, by the initial MRI images. In one approach this may be done manually, by cutting the resonator and/or moving it within a track until the desired behavior is achieved. As noted above, the passive resonator may be combined with slot antenna patterns on the surface by filling the slots with a suitable material.

In some embodiments, the passive resonator can include metamaterial elements such as capacitive and inductive components, and may have a size related to the RF wave length, $\lambda$. The resonators can be integrated within the dielectric liquid and/or at the surfaces and/or notches that surround the shell. In any of the foregoing embodiments, a passive resonator can be replaced by an active resonator as long as it serves to control the $B_1^+/B_1^-$ field homogeneity at the FOV. Resonators can also reside on the upper region of the transducer 200 with, for example, a polymeric topmost layer over the conductive layer $240_4$. When RF can penetrate the transducer exterior, such resonators, either passive or active, can affect the $B_1^+/B_1^-$ field homogeneity within the transducer at the FOV.

Certain embodiments of the present invention are described above. It is, however, expressly noted that the present invention is not limited to those embodiments; rather, additions and modifications to what is expressly described herein are also included within the scope of the invention.

What is claimed is:

1. An ultrasound transducer for use with an MRI unit having at least one transmit coil and at least one receive coil, the ultrasound transducer comprising:
   a dielectric layer; and
   conforming to at least a portion thereof, a first conductive layer having at least one passive resonator thereon or therethrough, the passive resonator having a geometry and dimensions selected to allow RF waves to penetrate the first conductive layer and rearrange a $B_1$ field inside the transducer to achieve an optimized $B_1^+$ and/or $B_1^-$ magnetic field distribution within a field of view of the MRI transmit and/or receive coil.

2. The ultrasound transducer of claim 1, wherein the optimized magnetic field distribution is maximal $B_1^+$ and/or $B_1^-$ homogeneity in a region of interest.

3. The ultrasound transducer of claim 1, wherein the optimized magnetic field distribution is maximal $B_1^+$ and/or $B_1^-$ sensitivity in a region of interest.

4. The ultrasound transducer of claim 1, wherein the at least one passive resonator is at least one elongated slot through the first conductive layer of the transducer and extending across at least a portion thereof.

5. The ultrasound transducer of claim 4, wherein the at least one slot is a pair of slots in a cruciform configuration.

6. The ultrasound transducer of claim 1, wherein the dielectric and first conductive layer are substantially hemispheric.

7. The ultrasound transducer of claim 1, further comprising a second conductive layer spaced apart from the first conductive layer but also conforming to the dielectric layer, wherein the dielectric layer is disposed between the first conductive layer and the second conductive layer in a multi-layer arrangement in a single transducer.

8. The ultrasound transducer of claim 5, wherein the at least one slot is filled with a metamaterial element.

9. The ultrasound transducer of claim 1 wherein a geometry, a location, and/or an orientation of the at least one passive resonator is adjustable to improve the $B_1^+$ and/or $B_1^-$ magnetic field distribution in a region of interest in response to one or more initial MRI images.

10. The ultrasound transducer of claim 9 wherein the at least one resonator is shaped as a loop, dipole, or figure-8.

11. The ultrasound transducer of claim 1, wherein the at least one passive resonator is disposed on an interior surface of the transducer at an interface with a dielectric medium.

12. The ultrasound transducer of claim 1, wherein the first conductive layer has at least two passive resonators thereon or therethrough.

13. The transducer of claim 12, wherein at least one passive resonator has a dielectric constant in excess of 10 and is attached to a surface of the transducer, and at least one passive resonator is at least one elongated slot through the first conductive layer of the transducer and extending across at least a portion thereof.

14. The transducer of claim 1, wherein the at least one passive resonator is disposed on an external area of the transducer.

15. The transducer of claim 14, wherein the external area is a bottom ring surface configured to surround a patient's head.

16. The transducer of claim 15, wherein the at least one passive resonator is a foil sheet or a mesh.

17. The transducer of claim 1, wherein
the first conductive layer comprises a two-element curved hemisphere including a domed top element and a bottom skirt element separated by an annular gap; and
the at least one passive resonator is a linear slot antenna configured to shift a region of $B_1^+$ and/or $B_1^-$ homogeneity toward a region of interest.

18. The transducer of claim 17, further comprising a conducting sheet slidably situated within guides to cover an adjustable amount of the linear slot antenna.

19. The transducer of claim 1, wherein:
the first conductive layer comprises a plurality of discrete conductive elements tiled in a mosaic configuration; and
the at least one passive resonator is a dipole antenna configured to shift a region of $B_1^+$ and/or $B_1^-$ homogeneity toward a region of interest.

20. The transducer of claim 19, further comprising a layer of adhesive or polymer under the dipole antenna to isolate the dipole antenna from the first conductive layer.

* * * * *